US009603899B2

(12) United States Patent
Mao et al.

(10) Patent No.: US 9,603,899 B2
(45) Date of Patent: Mar. 28, 2017

(54) PDGF INDUCED CELL HOMING

(75) Inventors: Jeremy J. Mao, Closter, NJ (US); Wenli Zhao, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/877,272

(22) PCT Filed: Oct. 3, 2011

(86) PCT No.: PCT/US2011/054646
§ 371 (c)(1),
(2), (4) Date: Nov. 8, 2013

(87) PCT Pub. No.: WO2012/045086
PCT Pub. Date: Apr. 5, 2012

(65) Prior Publication Data
US 2014/0050771 A1    Feb. 20, 2014

Related U.S. Application Data

(60) Provisional application No. 61/388,851, filed on Oct. 1, 2010.

(51) Int. Cl.
| | |
|---|---|
| A61K 38/18 | (2006.01) |
| A61F 13/00 | (2006.01) |
| A61F 2/00 | (2006.01) |
| C12N 5/00 | (2006.01) |
| C12N 5/0775 | (2010.01) |
| A61L 27/54 | (2006.01) |
| A61K 9/00 | (2006.01) |

(52) U.S. Cl.
CPC ............ *A61K 38/1858* (2013.01); *A61K 9/00* (2013.01); *A61L 27/54* (2013.01); *C12N 5/0068* (2013.01); *C12N 5/0663* (2013.01); *A61L 2300/414* (2013.01); *C12N 2501/105* (2013.01); *C12N 2501/135* (2013.01); *C12N 2501/15* (2013.01); *C12N 2501/21* (2013.01); *C12N 2533/40* (2013.01); *C12N 2533/54* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 8,106,008 B2 * | 1/2012 | Lynch et al. .................. | 514/8.2 |
| 2003/0129750 A1 | 7/2003 | Schwartz | |
| 2004/0258669 A1 | 12/2004 | Dzau et al. | |
| 2006/0110374 A1 | 5/2006 | Czeiger et al. | |
| 2008/0193426 A1 | 8/2008 | Kollet et al. | |
| 2010/0136085 A1 | 6/2010 | Hart et al. | |
| 2011/0038921 A1 * | 2/2011 | Wen et al. .................... | 424/445 |

FOREIGN PATENT DOCUMENTS

| | | |
|---|---|---|
| WO | WO 2006/116678 | 11/2006 |
| WO | WO 2008/094689 | 8/2008 |
| WO | WO 2009/055609 | 4/2009 |
| WO | WO 2009/134532 | 11/2009 |
| WO | WO 2010/148229 | * 12/2010 |

OTHER PUBLICATIONS

Agrawal et al., Epimorphic regeneration approach to tissue replacement in adult mammals, PNAS, 2010, pp. 3351-3355, vol. 107, No. 8.
Alpaslan et al., Long-term evaluation of recombinant human bone morphogenetic protein-2 induced bone formation with a biologic and synthetic delivery system, British J of Oral and Maxillofacial Surgery, 1996, pp. 414-418, vol. 34.
Bax et al., Bone Morphogenetic Protein-2 Increases the Rate of Callus Formation after Fracture of the Rabbit Tibia, Calcif Tissue Int., 1999, pp. 83-89, vol. 65.
Chamberlain et al., Concise Review: Mesenchymal Stem Cells: Their Phenotype, Differentiation Capacity, Immunological Features, and Potential for Homing, Stem Cells, 2007, pp. 2739-2749, vol. 25.
Galović Rengel et al., High efficiency entrapment of superoxide dismutase into mucoadhesive chitosan-coated liposomes, European J of Pharmaceutical Sciences, 2002, pp. 441-448, vol. 15.
Isobe et al., Bone Regeneration Produced in Rat Femur Defects by Polymer Capsules Containing Recombinant Human Bone Morphogenetic Protein-2, J Oral Maxillofac. Surg., 1999, pp. 695-698, vol. 57.
Jin et al., Nonfibrous Scaffolds Incorporating PDGF-BB Microspheres Induce Chemokine Expression and Tissue Neogenesis In Vivo, PLoS One, 2008, e1729, pp. 1-9, vol. 3, No. 3.
Kan et al., Integral Therapeutic Potential of Bone Marrow Mesenchymal Stem Cells, Current Drug Targets, 2005, pp. 31-41, vol. 6, No. 1.
Karp et al., Mesenchymal Stem Cell Homing: The Devil Is in the Details, Cell Stem Cell, 2009, pp. 206-216, vol. 4.
Kuboki et al., Two Distinctive BMP-Carriers Induce Zonal Chondrogenesis and Membranous Ossification, Respectively; Geometrical Factors of Matrices for Cell-Differentiation, Connective Tissue Research, 1995, pp. 219-226, vol. 32, Nos. 1-4.
Lee et al., Regeneration of the articular surface of the rabbit synovial joint by cell homing: a proof of concept study, Lancet, 2010, pp. 440-448, vol. 376.
Loetscher et al., Homing chemokines in rheumatoid arthritis, Arthritis Res., 2002, pp. 233-236, vol. 4, No. 4.
Murata et al., Carrier-dependency of cellular differentiation induced by bone morphogenetic protein in ectopic sites, Int. J. Oral Maxillofac. Surg., 1998, pp. 391-396, vol. 27.

(Continued)

*Primary Examiner* — Marianne P Allen
(74) *Attorney, Agent, or Firm* — Dentons US LLP

(57) ABSTRACT

Provided is a method of causing a cell to migrate to a scaffold. Also provided is a method of treating a mammal that has a tissue defect. Further provided is a tissue scaffold comprising platelet-derived growth factor (PDGF). Additionally, a method of making a tissue scaffold capable of recruiting a cell is provided.

15 Claims, 8 Drawing Sheets

(56) References Cited

OTHER PUBLICATIONS

Ozaki et al., Comprehensive Analysis of Chemotactic Factors for Bone Marrow Mesenchymal Stem Cells, Stem Cells and Development, 2007, pp. 119-129, vol. 16.

Phipps et al., Delivery of Platelet-Derived Growth Factor as a Chemotactic Factor for Mesenchymal Stem Cells by Bone-Mimetic Electrospun Scaffolds, PLoS One, 2012, e40831, pp. 1-9, vol. 7, No. 7.

Saito et al., New synthetic biodegradable polymers as BMP carriers for bone tissue engineering, Biomaterials, 2003, pp. 2287-2293, vol. 24.

Santos et al., Si—Ca—P xerogels and bone morphogenetic protein act synergistically on rat stromal marrow cell differentiation in vitro, J Biomed Mater Res, 1998, pp. 87-94, vol. 41.

Shi et al., Regulation of CXCR4 expression in human mesenchymal stem cells by cytokine treatment: role in homing efficiency in NOD/SCID mice, Haematologica, 2007, pp. 897-904, vol. 92, No. 7.

Sonoyama et al., Mesenchymal Stem Cell-Mediated Functional Tooth Regeneration in Swine, PLoS One, 2006, e79, pp. 1-8, vol. 1, No. 1.

Sordi et al., Bone marrow mesenchymal stem cells express a restricted set of functionally active chemokine receptors capable of promoting migration to pancreatic islets, Blood, 2005, pp. 419-427, vol. 106, No. 2.

Studier, Protein production by auto-induction in high-density shaking cultures, Protein Expression and Purification, 2005, pp. 207-234, vol. 41.

Sweeney et al., Repair of critical size rat calvarial defects using extracellular matrix protein gels, J Neurosurg, 1995, pp. 710-715, vol. 83.

Varde et al., Microspheres for controlled release drug delivery, Expert Opin. Biol. Ther., 2004, pp. 35-51, vol. 4, No. 1.

Viljanen et al., Low dosage of native allogeneic bone morphogenetic protein in repair of sheep calvarial defects, J Oral Maxillofac. Surg., 1997, pp. 389-393, vol. 26.

Wagner et al., The Crossflow Injection Technique: An Improvement of the Ethanol Injection Method, J Liposome Research, 2002, pp. 259-270, vol. 12, No. 3.

Zhang et al., A role for the polysialic acid—neural cell adhesion molecule in PDGF-induced chemotaxis of oligodendrocyte precursor cells, J Cell Science, 2003, pp. 93-103, vol. 117, No. 1.

\* cited by examiner

▨ Alginate with gelatin μ-spheres
(SDF1/TGFβ3/IGF1/PDGFBB)

▨ PLGA disk

FIG. 6A-B
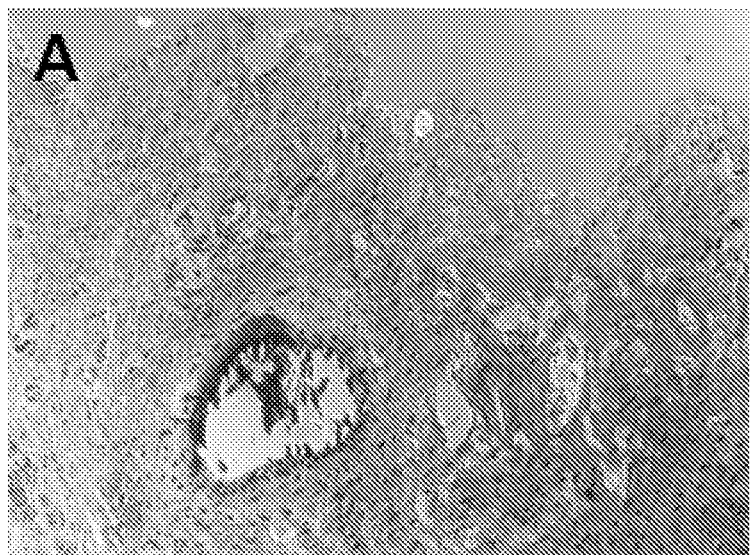
Scaffold 1
Scaffold 2

Scaffold 3

PDGF INDUCED CELL HOMING

CROSS-REFERENCE TO RELATED APPLICATIONS

The present application claims the benefit of priority to PCT International Application No. PCT/US11/54646 filed Oct. 3, 2011, which claims the benefit U.S. Provisional Application Ser. No. 61/388,851 filed Oct. 1, 2010, each of which is incorporated herein by reference in their entireties.

STATEMENT REGARDING FEDERALLY SPONSORED RESEARCH OR DEVELOPMENT

This invention was made with government support under R01DE018248 awarded by the National Institutes of Health. The government has certain rights in the invention.

MATERIAL INCORPORATED-BY-REFERENCE

Not Applicable.

FIELD OF THE INVENTION

The present invention generally relates to cell homing and tissue regeneration.

BACKGROUND OF THE INVENTION

Progenitor cells have been harvested from multiple adult tissues, and transplanted for tissue regeneration. Despite its scientific validity, cell transplantation has associated economic and regulatory challenges in clinical translation including immune rejection, pathogen transmission, potential tumorigenesis, packaging/storage/shipping, and difficulties in clinical adoption and regulatory approval. Tissue regeneration by recruiting the host's endogenous cells, including progenitor cells, has been discussed in the art (see e.g., Agrawal et al. 2010 PNAS 107, 3351-3355). The ability of various cells, including MSCs, to migrate and home to various organs is well-established. (see e.g., Chamberlain et al., 2007, Stem Cells 25:2739-2749; Kan et al., 2005, Current Drug Targets 6:31-41; Loetscher and Moser, 2002, Arthritis Res. 4:233-236; Shi, M. et al., 2007, Haematologica 92:897-904; Sordi, V. et al., 2005, Blood 106:419-427; U.S. Patent Application Publication US 2003/0129750 A1; U.S. Patent Application Publication US 2004/0258669 A1; U.S. Patent Application Publication US 2006/0110374 A1; U.S. Patent Application Publication US 2008/0193426 A1; PCT Patent Publication WO 2008/094689 A2).

PDGF is a growth factor (i.e., a protein) that plays a role in embryonic development, cell proliferation, cell migration, and angiogenesis. Naturally occurring PDGF is a dimeric glycoprotein composed of two A (-AA) or two B (-BB) chains or a combination of the two (-AB).

SUMMARY OF THE INVENTION

Among the various aspects of the present invention is the provision of a method for tissue regeneration that involves using a subject's endogenous progenitor cells to regenerate damaged tissue in vivo.

One aspect provides a method of causing a cell to migrate to a scaffold. In some embodiments, the method includes placing a scaffold comprising an effective amount of platelet-derived growth factor (PDGF) in fluid communication with a cell. In some embodiments of the method, the scaffold does not comprise a transplanted cell. In some embodiments, the effective amount of PDGF induces migration of the cell into the scaffold.

Another aspect provides a method of treating a subject having a tissue or organ defect. In some embodiments, the method includes implanting a scaffold comprising an effective amount of PDGF at or near a tissue or organ defect. In some embodiments of the method, the scaffold does not comprise a transplanted cell prior to implant. In some embodiments, the effective amount of PDGF induces migration of a cell into the scaffold.

In some embodiments, the migrating cell is a progenitor cell. In some configurations, the migrating cell is an alveolar stem cell.

In some embodiments, PDGF includes at least one of PDGF-AA, PDGF-BB, and PDGF-AB. In some configurations, the PDGF includes PDGF-BB.

In some embodiments, PDGF is present in the scaffold at a concentration of about 1 ng/gram scaffold to about 30,000 ng/gram scaffold. In some configurations, the scaffold includes composition containing PDGF at a concentration of about 1 ng/ml to about 100 ng/ml. In some configurations the scaffold includes composition containing PDGF at a concentration of about 50 ng/ml.

In some embodiments, the scaffold is implanted at a site of a tissue or organ defect in the subject.

In some embodiments, the scaffold includes at least two layers. In some embodiments, the scaffold includes at least one layer comprising PDGF. In some embodiments, the scaffold includes a first layer and a second layer, the first layer comprises an alginate and PDGF and the second layer comprises PLGA.

In some embodiments, PDGF is encapsulated in a microsphere.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 2A shows dose-dependent migration. FIG. 2B shows PDGF-BB was the most potent chemoattractant among all PDGF isoforms. *p<0.05. Negative control or NC: serum-free medium; positive control or PC: DMEM with 15% FBS. FIG. 2C shows expression of PDGF receptors in alveolar stem/progenitor cells. Grey line: fluorescent intensity of unstained cells; black line: the fluorescent intensity of cells labeled with specific antigen.

FIG. 4A is a cartoon depicting a bilayered scaffold fabricated with a bottom poly(lactide-co-glycolic acid) (PLGA) layer and a top alginate layer containing gelatin microspheres that slow-release SDF1, TGFβ3, IGF1 and PDGFBB. FIG. 4B is an image showing a scaffold implanted in the subcutaneous nasal dorsum of a 12 week old Sprague Dawley rats and harvested after 10 weeks of implantation.

FIG. 6 is a series of images showing cell recruitment into scaffolds. FIG. 6A shows Scaffold 1. FIG. 6B shows Scaffold 2.

FIG. 7A shows Scaffold 1 and cartilage specific markers for aggrecan. FIG. 7B shows Scaffold 2 and cartilage specific markers for aggrecan. FIG. 7C shows Scaffold 3 and cartilage specific markers for aggrecan. FIG. 7D shows scaffold 1 and cartilage specific markers for Type II Collagen. FIG. 7E shows Scaffold 2 and cartilage specific markers for Type II Collagen. FIG. 7F shoes Scaffold 3 and cartilage specific markers for Type II Collagen.

DETAILED DESCRIPTION OF THE INVENTION

Figure 1:
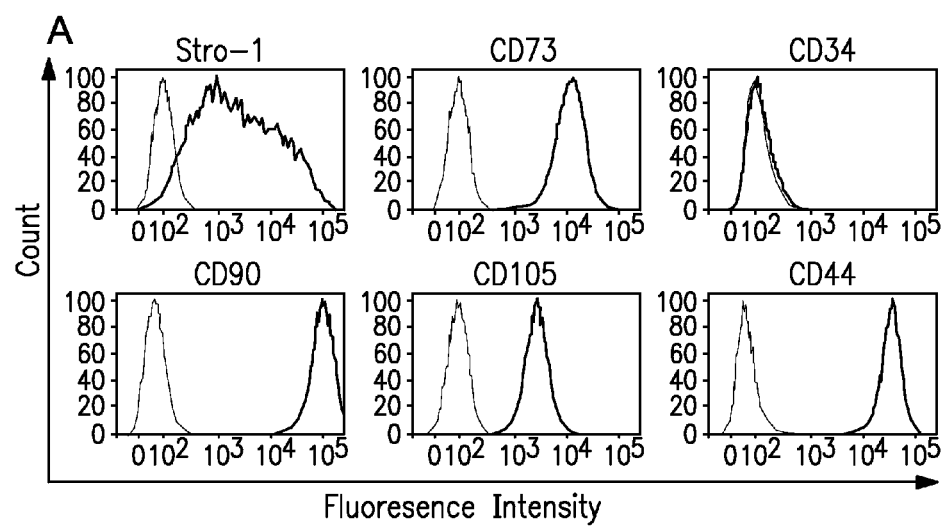
FIG. 1 is a series of line plots and a series of images showing characterization of alveolar stem/progenitor cells by FACS (FIG. 1A) and multipotentiality including (FIG. 1B) osteogenesis (von Kossa), (FIG. 1C) adipogenesis (Oil-red O), (FIG. 1D) chondrogenesis (safarin O) and (FIG. 1E) myogenesis (myosin heavy chain).
Figure 1:
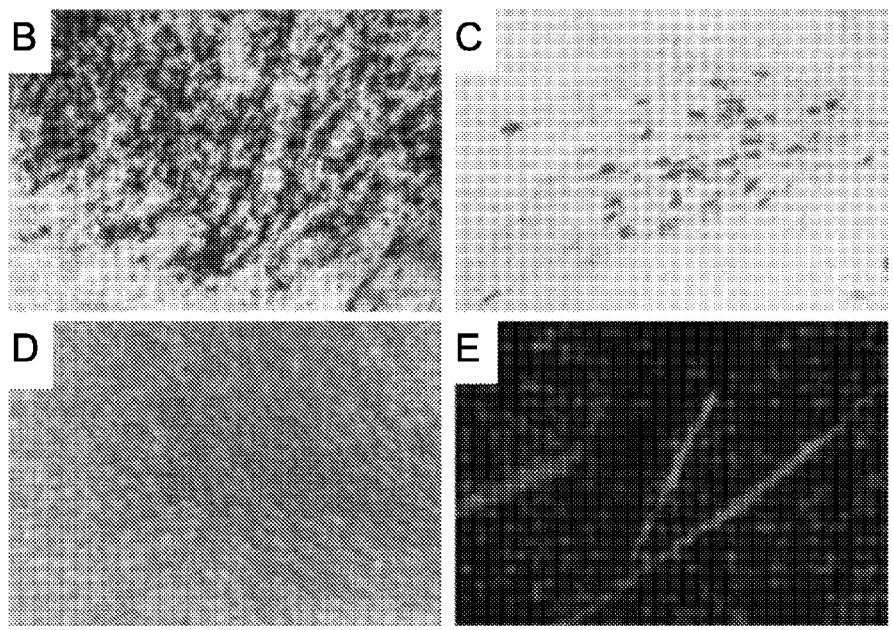

The present disclosure is based at least in part on the observation that that platelet-derived growth factor (PDGF) induces the homing of progenitor cells such as adult bone marrow stem cells. These findings demonstrate inducing the recruitment of endogenous or transplanted progenitor cells towards tissue regeneration. Thus, scaffolds that comprise PDGF are useful for tissue regeneration.

Described herein are studies characterizing PDGF's ability to recruit progenitor cells, such as alveolar bone stem cells, in a dose-response manner. As shown herein, all PDGF isoforms were capable of recruiting alveolar stem/progenitor cells (see Example 1). Furthermore, PDGF-BB showed the most robust efficacy, which was equal to positive control group with 15% fetal bovine serum. Progenitor cells such as adult alveolar stem cells are multipotent, with capacity to differentiate into, for example, osteoblasts, chondrocytes, adipocytes, myocytes and endothelial-like cells. Thus, PDGF (e.g., PDGF-BB) can be used to recruit progenitor cells for regeneration of tissues such as bone, cartilage, muscle, adipose, blood vessels, dental pulp, dentin, and the entire tooth.

Various embodiments provide a method for tissue regeneration that involves using a subject's endogenous progenitor cells to regenerate damaged tissue in vivo. Platelet-derived growth factors (PDGF) can be used to induce homing of progenitor cells, such as alveolar bone stem cells, to regenerate tissues such as dental pulp, dentin, and teeth, and derive other types of tissue, such as bone, cartilage, muscle, adipose, and blood vessels. Such methods can reduce challenges associated with regulatory and clinical translation by using host cells to regenerate the tissues in the subject, rather than transplanting or delivering harvested cells to the subject.

PDGF

Various compositions and methods described herein include platelet-derived growth factor (PDGF). PDGF as described herein can be selected from one or more of: PDGF-AA, PDGF-BB, PDGF-CC, PDGF-DD, and PDGF-AB. For example, PDGF can be one or more of: PDGF-AA, PDGF-BB, and PDGF-AB. As shown herein, while all types of PDGF-AA, PDGF-BB, and PDGF-AB resulted in cell migration, PDGF-BB showed higher rates of cell migration (see Example 1).

PDGF can have the amino acid sequence of a naturally occurring PDGF from any mammalian species, including humans. Alternatively, the PDGF can have the amino acid sequence modified from a naturally occurring PDGF provided the PDGF has substantially the same activity of the naturally occurring protein. The skilled artisan can identify numerous such derivatives of PDGF without undue experimentation. In some embodiments, the PDGF can have the amino acid sequence of the human PDGF. For example, human PDGF can have an amino acid sequence according to GenBank Accession Number AAA60552.1. PDGF is commercially available from a variety of manufactures.

PDGF present in a composition describe herein at any concentration. In some embodiments, PDGF is present in the scaffold at a concentration of about 1 ng/ml to about 1,000 ng/ml scaffold. As an example, As another example, PDGF can be present at a concentration of about 100 ng/ml, about 150 ng/ml, about 200 ng/ml, about 250 ng/ml, about 300 ng/ml, about 400 ng/ml, about 450 ng/ml, about 500 ng/ml, about 550 ng/ml, about 600 ng/ml, about 650 ng/ml, or about 700 ng/ml. As another example, PDGF can be present in the scaffold at a concentration of about 10 ng/ml to about 100 ng/ml. As another example, PDGF can be present in the scaffold at a concentration of about 10 ng/ml to about 50 ng/ml. As another example, PDGF can be present in the scaffold at a concentration of about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, or about 100 ng/ml. As shown herein, cell migration was shown for PDGF concentrations of 10 ng/ml, 25 ng/ml, and 50 ng/ml, where highest cell migration was observed at 50 ng/ml (see Example 1).

PDGF present in a scaffold described herein at any concentration. In some embodiments, PDGF is present in the scaffold at a concentration of about 1 ng/gram scaffold to about 30,000 ng/gram scaffold. For example, PDGF can be present in the scaffold at a concentration of about 10 ng/gram scaffold to about 3,000 ng/gram scaffold. As another example, PDGF can be present in the scaffold at a concentration of about 10 ng/gram scaffold to about 300 ng/gram scaffold. As another example, PDGF can be present in the scaffold at a concentration of about 200 ng/gram scaffold to about 500 ng/gram scaffold. As another example, PDGF can be present in the scaffold at a concentration of about 300 ng/gram scaffold.

Because different scaffold materials allow release of a given amount of PDGF at a different rate, it is also useful to measure the "potency" of the growth factor by how much growth factor is released in a given period of time, e.g., a week. In some embodiments, PDGF is released at a rate of about 1 to 1000 ng/gram of scaffold. For example, PDGF can be released at a rate of about 10 to 100 ng/gram of scaffold.

Progenitor Cells

Various compositions and methods described herein provide for recruitment of a progenitor cell or inducing migration of a progenitor cell. A progenitor cell is a cell that is undifferentiated or partially undifferentiated, and can divide and proliferate to produce undifferentiated or partially undifferentiated cells or can differentiate to produce at least one differentiated or specialized cell. A progenitor cell can be a pluripotent cell, which means that the cell is capable of self-renewal and of trans-differentiation into multiple tissue types upon differentiation. Pluripotent progenitor cells include stem cells, such as embryonic stem cells and adult stem cells. A progenitor cell can be a multipotent cell. A progenitor cell can be self-renewing. For example, the progenitor cell can be a stem cell. As another example, the progenitor cell can be an adult stem cell. As another example, the progenitor cell can be an adult alveolar bone stem cell. As another example, the progenitor cell can be a human adult alveolar bone stem cell. Alveolar bone stem cell can be derived from neural crest cells. In some embodiments, a progenitor cell can differentiate into, or otherwise form, osteoblasts, chondrocytes, adipocytes, myocytes or endothelial-like cells.

Progenitor cells can be isolated, purified, or cultured by a variety of means known to the art Methods for the isolation and culture of progenitor cells are discussed in, for example, Vunjak-Novakovic and Freshney (2006) Culture of Cells for Tissue Engineering, Wiley-Liss, ISBN-10 0471629359.

A progenitor cell can be comprised of, or derived from, an animal, including, but not limited to, mammals, reptiles, and avians, more preferably horses, cows, dogs, cats, sheep, pigs, and chickens, and most preferably human.

Scaffold and Matrix Material

Various embodiments of the compositions and methods described herein employ a scaffold comprising PDGF. A scaffold can be fabricated with any matrix material recognized as useful by the skilled artisan. A matrix material can be a biocompatible material that generally forms a porous, microcellular scaffold, which provides a physical support for cells migrating thereto. Such matrix materials can: allow cell attachment and migration; deliver and retain cells and biochemical factors; enable diffusion of cell nutrients and expressed products; or exert certain mechanical and biological influences to modify the behavior of the cell phase. The matrix material generally forms a porous, microcellular scaffold of a biocompatible material that provides a physical support and an adhesive substrate for recruitment and growth of cells during in vitro or in vivo culturing.

Suitable scaffold and matrix materials are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X. For example, matrix materials can be, at least in part, solid xenogenic (e.g., hydroxyapatite) (Kuboki et al. 1995 Connect Tissue Res 32, 219-226; Murata et al. 1998 Int J Oral Maxillofac Surg 27, 391-396), solid alloplastic (polyethylene polymers) materials (Saito and Takaoka 2003 Biomaterials 24 2287-93; Isobe et al. 1999 J Oral Maxillofac Surg 57, 695-8), or gels of autogenous (Sweeney et al. 1995. J Neurosurg 83, 710-715), allogenic (Bax et al. 1999 Calcif Tissue Int 65, 83-89; Viljanen et al. 1997 Int J Oral Maxillofac Surg 26, 389-393), or alloplastic origin (Santos et al. 1998. J Biomed Mater Res 41, 87-94), and combinations of the above (Alpaslan et al. 1996 Br J of Oral Maxillofac Surg 34, 414-418).

The matrix comprising the scaffold can have an adequate porosity and an adequate pore size so as to facilitate cell recruitment and diffusion throughout the whole structure of both cells and nutrients. The matrix can be biodegradable providing for absorption of the matrix by the surrounding tissues, which can eliminate the necessity of a surgical removal. The rate at which degradation occurs can coincide as much as possible with the rate of tissue or organ formation. Thus, while cells are fabricating their own natural structure around themselves, the matrix is able to provide structural integrity and eventually break down, leaving the neotissue, newly formed tissue or organ which can assume the mechanical load. The matrix can be an injectable matrix in some configurations. The matrix can be delivered to a tissue using minimally invasive endoscopic procedures.

The scaffold can comprise a matrix material having different phases of viscosity. For example, a matrix can have a substantially liquid phase or a substantially gelled phase. The transition between phases can be stimulated by a variety of factors including, but limited to, light, chemical, magnetic, electrical, and mechanical stimulus. For example, the matrix can be a thermosensitive matrix with a substantially liquid phase at about room temperature and a substantially gelled phase at about body temperature. The liquid phase of the matrix can have a lower viscosity that provides for optimal distribution of growth factors or other additives and injectability, while the solid phase of the matrix can have an elevated viscosity that provides for matrix retention at or within the target tissue.

Figure 4:
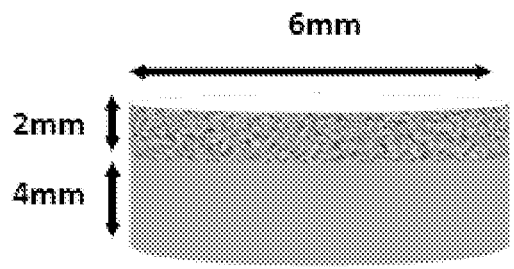
FIG. 4 is a cartoon and an image showing bilayered scaffolds.
Figure 4:
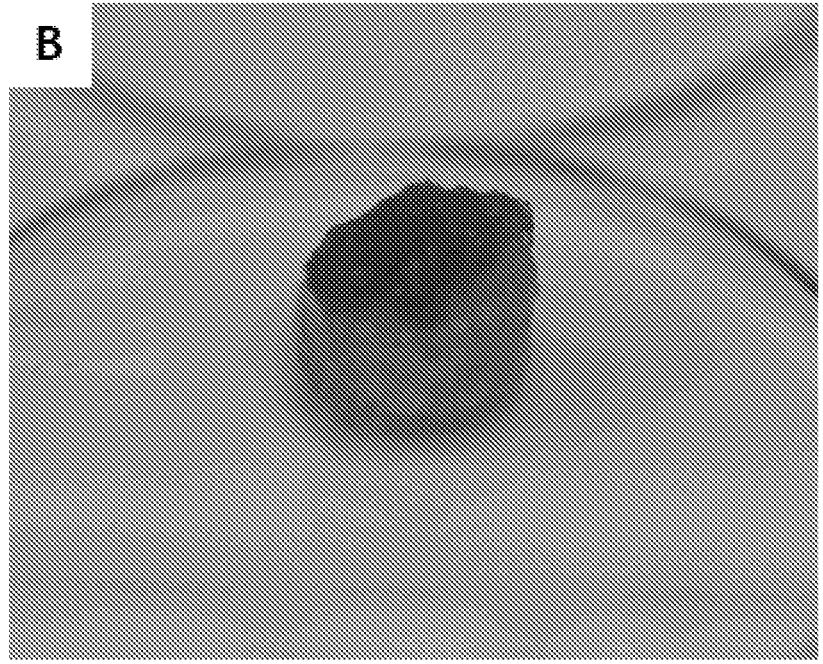

The scaffold can comprise one or more layers, each with the same or different matrix materials. For example, a scaffold can comprises at least two layers, at least three layers, at least four layers, or more. As another example, a scaffold can comprise a first layer comprising a first matrix material and a second layer comprising a second matrix material. As another example, a scaffold can comprise a first layer comprising a alginate and a second layer comprising a PLGA. An agent for inducing the recruitment of progenitor cells (e.g., PDGF) can be included in one or more layers of a multi-layered scaffold. For example, a PDGF (e.g., PDGF-BB) can be included in the alginate layer of a scaffold also including a PLGA layer (see e.g., FIG. 4). As another, a PDGF (e.g., PDGF-BB) can be included in multiple layers of a scaffold.

The scaffold can comprise a matrix material formed of synthetic polymers. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations and derivatives of the above. Alternatively, the matrix can be formed of naturally occurring biopolymers. Such naturally occurring biopolymers or bio-copolymers include, but are not limited to, fibrin, fibrinogen, fibronectin, collagen, alginate, and other suitable biopolymers. Also, the matrix can be formed from a mixture of naturally occurring biopolymers and synthetic polymers.

The scaffold can include one or more matrix materials including, but not limited to, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, polyacrylate, or a polyethylene oxide-polypropylene glycol block copolymer. Matrices can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, or nylon.

The scaffold can further comprise any other bioactive molecule, for example an antibiotic or an additional chemotactic growth factor or another osteogenic, dentinogenic, amelogenic, or cementogenic growth factor. In some embodiments, the scaffold is strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation.

The concentration of compound in the scaffold will vary with the nature of the compound, its physiological role, and desired therapeutic or diagnostic effect. A therapeutically effective amount is generally a sufficient concentration of therapeutic agent to display the desired effect without undue toxicity. For example, the matrix can include PDGF at the above described concentrations. The compound can be incorporated into the scaffold or matrix material by any known method. In some embodiments, the compound is imbedded in a gel, e.g., a collagen gel incorporated into the pores of the scaffold or matrix material.

Alternatively, chemical modification methods can be used to covalently link the compound to a matrix material. The surface functional groups of the matrix can be coupled with reactive functional groups of the compound to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

Pores and channels of the scaffold can be engineered to be of various diameters. For example, the pores of the scaffold can have a diameter range from micrometers to millimeters. In some embodiments, the pores of the matrix material include microchannels. Microchannels generally have an average diameter of about 0.1 µm to about 1,000 µm, e.g., about 50 µm to about 500 µm (for example about 100 µm, 150 µm, about 200 µm, about 250 µm, about 300 µm, about 350 µm, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the matrix material(s). In other embodiments, microchannels are engineered to occur in the matrix materials.

Several methods can be used for fabrication of porous scaffolds, including particulate leaching, gas foaming, electrospinning, freeze drying, foaming of ceramic from slurry, and the formation of polymeric sponge. Other methods can be used for fabrication of porous scaffolds include computer aided design (CAD) and synthesizing the scaffold with a bioplotter (e.g., solid freeform fabrication) (e.g., Bioplotter™, EnvisionTec, Germany).

Biologic drugs that can be added to the compositions of the invention include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner that enhances a particular desired therapeutic effect, for example, the cytolysis of bacterial cells or the growth of tissue- or organ-specific cells or vascularization. Biologic drugs can also be incorporated directly into the matrix component. Those of skill in the art will know, or can readily ascertain, other substances which can act as suitable non-biologic and biologic drugs.

Compositions described herein can also be modified to incorporate a diagnostic agent, such as a radiopaque agent. The presence of such agents can allow the physician to monitor the progression of wound healing occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents that can be utilized in the compositions can be readily ascertained by those of skill in the art and can include, for example, the use of radiolabeled fatty acids or analogs thereof.

The concentration of an agent in the composition will vary with the nature of the compound, its physiological role, and desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the tissue graft, while minimizing potential toxicity. In any event, the desired concentration in a particular instance for a particular compound is readily ascertainable by one of skill in the art.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, preferably in purified form, together with a suitable amount of carrier so as to provide the form for proper administration to the subject.

The formulation should suit the mode of administration. The agents of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Encapsulation

The compound can alternatively be introduced into or onto the matrix via a carrier based system, such as an encapsulation vehicle. For example, PDGF can be encapsulated within a polymeric delivery systems so as to provide for controlled release of tissue growth factor from within the matrix. Such vehicles are useful as slow release compositions. For example, growth factors can be micro-encapsulated to provide for enhanced stability or prolonged delivery. Encapsulation vehicles include, but are not limited to, microparticles, liposomes, microspheres, or the like, or a combination of any of the above to provide the desired release profile in varying proportions. Other methods of controlled-release delivery of agents will be known to the skilled artisan. Moreover, these and other systems can be combined or modified to optimize the integration/release of agents within the matrix.

For example, the polymeric delivery system can be a polymeric microsphere, preferably a PLGA polymeric microspheres. A variety of polymeric delivery systems, as well as methods for encapsulating a molecule such as a growth factor, are known to the art (see e.g., Varde and Pack (2004) Expert Opin Biol Ther 4, 35-51). Polymeric microspheres can be produced using naturally occurring or synthetic polymers and are particulate systems in the size range of 0.1 to 500 µm. Polymeric micelles and polymeromes are polymeric delivery vehicles with similar characteristics to microspheres and can also facilitate encapsulation and matrix integration of the compounds described herein. Fabrication, encapsulation, and stabilization of microspheres for a variety of payloads are within the skill of the art (see e.g., Varde & Pack (2004) Expert Opin. Biol. 4(1) 35-51). The release rate of the microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme).

Liposomes can also be used to integrate compounds with the matrix. The agent carrying capacity and release rate of liposomes can depend on the lipid composition, size, charge, drug/lipid ratio, and method of delivery. Conventional liposomes are composed of neutral or anionic lipids (natural or synthetic). Commonly used lipids are lecithins such as phosphatidylcholines, phosphatidylethanolamines, sphingomyelins, phosphatidylserines, phosphatidylglycerols, and phosphatidylinositols. Liposome encapsulation methods are commonly known in the arts (Galovic et al. (2002) Eur. J. Pharm. Sci. 15, 441-448; Wagner et al. (2002) J. Liposome Res. 12, 259-270). Targeted liposomes and reactive liposomes can also be used in combination with the agents and matrix. Targeted liposomes have targeting ligands, such as monoclonal antibodies or lectins, attached to their surface, allowing interaction with specific receptors and/or cell types. Reactive or polymorphic liposomes include a wide range of liposomes, the common property of which is their tendency to change their phase and structure upon a particular interaction (e.g., pH-sensitive liposomes) (see e.g., Lasic (1997) Liposomes in Gene Delivery, CRC Press, FL).

Method

Various embodiments provide a method to recruit, home, or induce differentiation of progenitor cells, such as host alveolar bone stem cells, by using PDGF.

As shown herein, alveolar bone marrow (derived from neural crest cells) was obtained from alveolar bone samples, mononucleated and adherent cells were isolated and cultured in culture medium; treated with defined media to induce osteogenesis, adiopogenesis, chondrogenesis, and myogenesis; and then induced for endothelial progenitor cells. Transwell migration assays showed that PDGF induced dose-dependent migration for host progenitor cells. Thus is shown that progenitor cells, such as adult alveolar stem cells, can be recruited into a scaffold and induced to differentiate into cells such as osteoblasts, chondrocytes, adipocytes, myocytes, and endothelial-like cells.

In some embodiments, methods of causing a cell to migrate to a scaffold are provided. The method can include placing a scaffold containing PDGF in fluid communication with cells. As used herein, a scaffold is in "fluid communication" with a cell if the cell has no physical barrier (e.g., a basement membrane, areolar connective tissue, adipose connective tissue, etc.) preventing the cell from migrating to the scaffold. Without being bound to any particular mechanism, it is believed that the cell migrates to the scaffold along a moist path from its source, in response to the presence of PDGF forming a concentration gradient to the cell, and thereby influencing the cell to migrate toward the higher concentrations of PDGF in the scaffold.

The scaffold optionally does not comprise a transplanted mammalian cell, i.e., no cell is applied to the scaffold; any cell present in the scaffold migrated into the scaffold.

These methods are not narrowly limited to recruitment of any particular cell type. In particular, the methods are useful for recruiting any undifferentiated or differentiated cells in the MSC lineage, for example osteoblasts, chondrocytes, myocytes, adipocytes, or endothelial cells. For example, the cell can be a progenitor cell as discussed above.

A scaffold is generally understood to be a three-dimensional structure into which cells, tissue, vessels, etc., can grow into, colonize and populate when the scaffold is placed into a tissue site. A scaffold of the method can be as discussed herein.

Implanting

The compositions and methods described herein hold significant clinical value because of their ability to be recruit endogenous progenitor cells, thereby optionally avoiding transplant of cells to a subject. A determination of the need for treatment will typically be assessed by a history and physical exam consistent with the tissue or organ defect at issue. A subject in need of the therapeutic methods and compositions described herein can be a subject having, diagnosed with, suspected of having, or at risk for developing a tissue or organ defect. Diagnosis of the various conditions treatable by the methods described herein is within the skill of the art. The subject is preferably an animal, including, but not limited to, mammals, reptiles, and avians, more preferably horses, cows, dogs, cats, sheep, pigs, and chickens, and most preferably human.

The subject can be an animal subject, including, but not limited to, mammals, reptiles, and avians, more preferably horses, cows, dogs, cats, sheep, pigs, mice, rats, monkeys, guinea pigs, and chickens, and most preferably a human.

An effective amount of a composition comprising PDGF or a scaffold containing a composition comprising PDGF described herein is generally that which can recruit and induce migration of a sufficient number of cells, such as progenitor cells, to increase biological function of a tissue or organ.

As an example, a subject in need can have a deficiency of a particular cell type of at least about 5%, about 10%, about 25%, about 50%, about 75%, about 90% or more of a particular cell type, and the method can provide an increase in number or function of the particular cell type. As another example, a subject in need can have damage to a tissue or organ, and the method can provide an increase in biological function of the tissue or organ by at least about 5%, about 10%, about 25%, about 50%, about 75%, about 90%, about 100%, or about 200%, or even by as much as about 300%, about 400%, or about 500%. As yet another example, the subject in need can have a disease, disorder, or condition, and the method provides an engineered scaffold sufficient that can recruit progenitor cells and form tissue sufficient to ameliorate or stabilize the disease, disorder, or condition. For example, the subject can have a disease, disorder, or condition that results in the loss, atrophy, dysfunction, and/or death of cells. Exemplary treated conditions include a neural, glial, or muscle degenerative disorder, muscular atrophy or dystrophy, heart disease such as congenital heart failure, hepatitis or cirrhosis of the liver, an autoimmune disorder, diabetes, cancer, a congenital defect that results in the absence of a tissue or organ, or a disease, disorder, or condition that requires the removal of a tissue or organ, ischemic diseases such as angina pectoris, myocardial infarction and ischemic limb, and/or accidental tissue defect or damage such as fracture or wound. In a further example, the subject in need can have an increased risk of developing a disease, disorder, or condition that is delayed or prevented by the method.

The tissue or organ can be selected from bladder, brain, nervous tissue, glia, esophagus, fallopian tube, heart, pancreas, intestines, gall bladder, kidney, liver, lung, ovaries, prostate, spinal cord, spleen, stomach, testes, thymus, thyroid, trachea, urogenital tract, ureter, urethra, uterus, breast, skeletal muscle, skin, adipose, tooth, bone, and cartilage. Progenitor cells can be from the same subject into which the engineered tissue composition is grafted. Alternatively, the progenitor cells can be from the same species, or even different species.

Implantation of an engineered construct is within the skill of the art. The scaffold or matrix material can be either fully or partially implanted into a tissue or organ of the subject to become a functioning part thereof. Preferably, the implant initially attaches to and communicates with the host through a cellular monolayer. Over time, endogenous cells can migrate into the scaffold to form tissue. The cells surrounding the engineered tissue can be attracted by biologically active materials, including biological response modifiers, such as polysaccharides, proteins, peptides, genes, antigens, and antibodies, which can be selectively incorporated into the matrix to provide the needed selectivity, for example, to tether the cell receptors to the matrix, stimulate cell migration into the matrix, or both. The matrix can comprise a gelled phase and interconnecting channels that allow for cell migration, augmented by both biological and physical-chemical gradients. For example, cells surrounding the implanted seeded matrix can be attracted by biologically active materials including PDGF. One of skill in the art will recognize and know how to use other biologically active materials that are appropriate for attracting cells to the matrix.

The methods, compositions, and devices of the invention can include concurrent or sequential treatment with one or more of enzymes, ions, growth factors, and biologic agents, such as thrombin and calcium, or combinations thereof. The methods, compositions, and devices of the invention can include concurrent or sequential treatment with non-biologic and/or biologic drugs.

When used in the treatments described herein, a therapeutically effective amount of PDGF can be employed in pure form or, where such forms exist, in pharmaceutically acceptable salt form and with or without a pharmaceutically acceptable excipient. For example, the compounds of the invention can be administered, at a reasonable benefit/risk ratio applicable to any medical treatment, in a sufficient amount to increase biological function of a tissue or organ.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present invention will be decided by an attending physician within the scope of sound medical judgment.

Administration of compositions or scaffold comprising compositions described herein can occur as a single event or over a time course of treatment. For example, administration can be daily, weekly, bi-weekly, or monthly.

Treatment in accord with the methods described herein can be performed prior to, concurrent with, or after conventional treatment modalities for a tissue or organ defect. Compositions or scaffold comprising compositions described herein can be administered simultaneously or sequentially with another agent, such as an antibiotic, an antiinflammatory, or another agent. For example, a administration can occur simultaneously with another agent, such as an antibiotic or an anti-inflammatory.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions comprising PDGF, scaffolds, or matrix materials. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Small alveolar bone samples were obtained from multiple healthy adult donors under IRB approval. Alveolar bone marrow was selected because 1) it is understudied, and 2) it derives from neural crest cells in development. Mononucleated and adherent cells of alveolar bone marrow were isolated and cultured in DMEM supplemented 15% FBS, 100 U/mL penicillin-streptomycin. Early passage cells (P3-P5) were analyzed for the expression of Stro-1, CD105, Cd44, CD73, CD90 and CD34 by both antibody immunocytochemistry and FACS. To test multipotenciality, cells were treated with chemically defined media for osteogenesis, adipogenesis, chondrogenesis and myogenesis. Cells were further induced towards endothelial progenitor cells and examined for capilary tube formation in vitro. Transwell migration assay was performed to determine PDGF's ability to recruit alveolar stem/progenitor cells in a dose-response manner.

Figure 2:
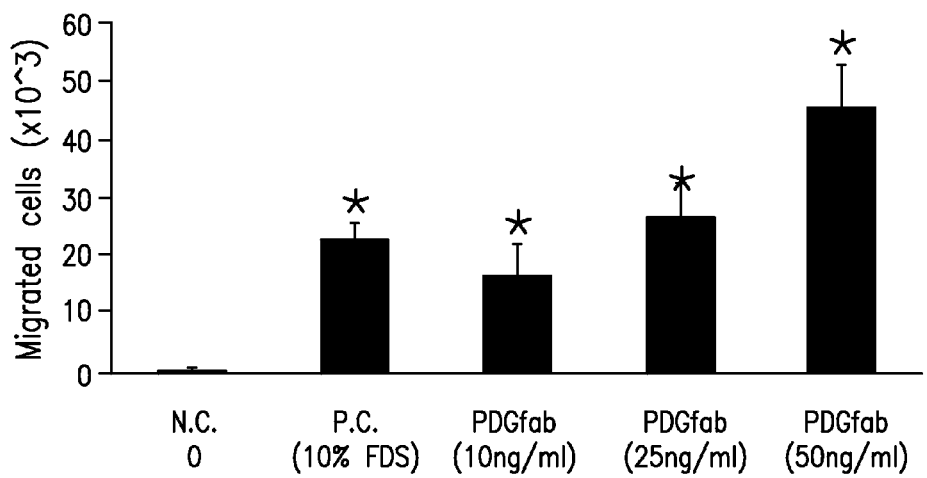
FIG. 2 is a series of bar graphs and line plots showing PDGF-induced recruitment of alveolar stem/progenitor cells.
Figure 2:
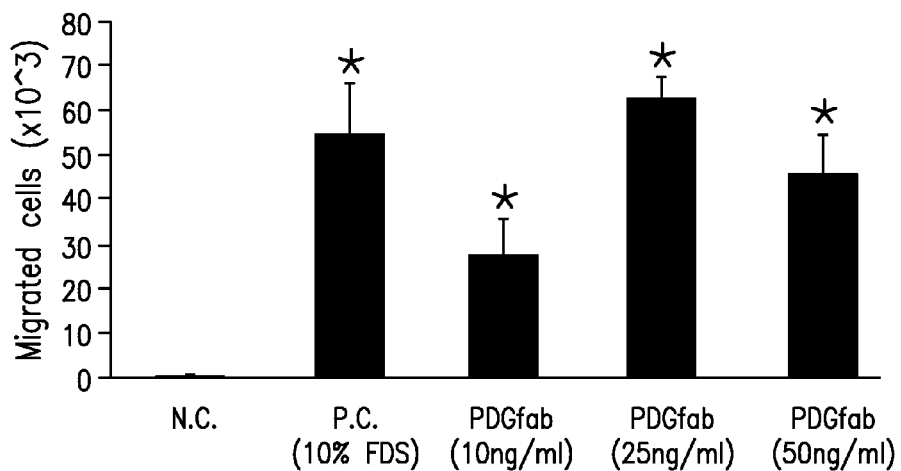
Figure 2:
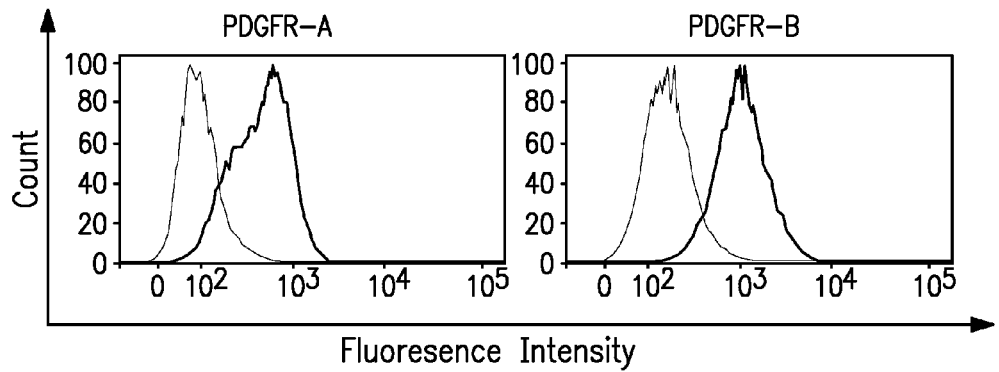
Figure 3:
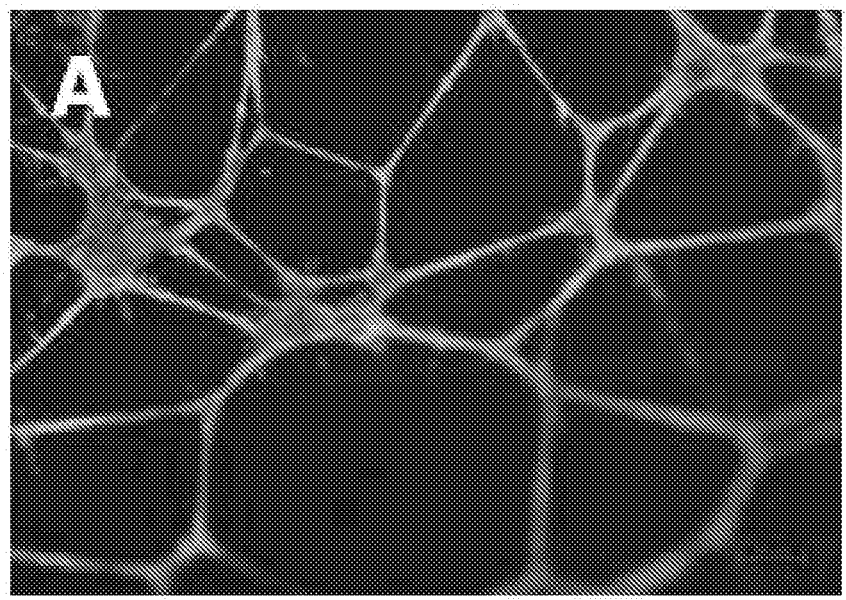
FIG. 3 is a pair of images showing capillary tube formation by alveolar stem/progenitor cells. In chemically defined medium, alveolar stem/progenitor cells differentiated into classic capillary tubular structures labeled with calcein AM (FIG. 3A). Tubular formation was blocked by 15 μM sulforaphane (FIG. 3B).
Figure 3:
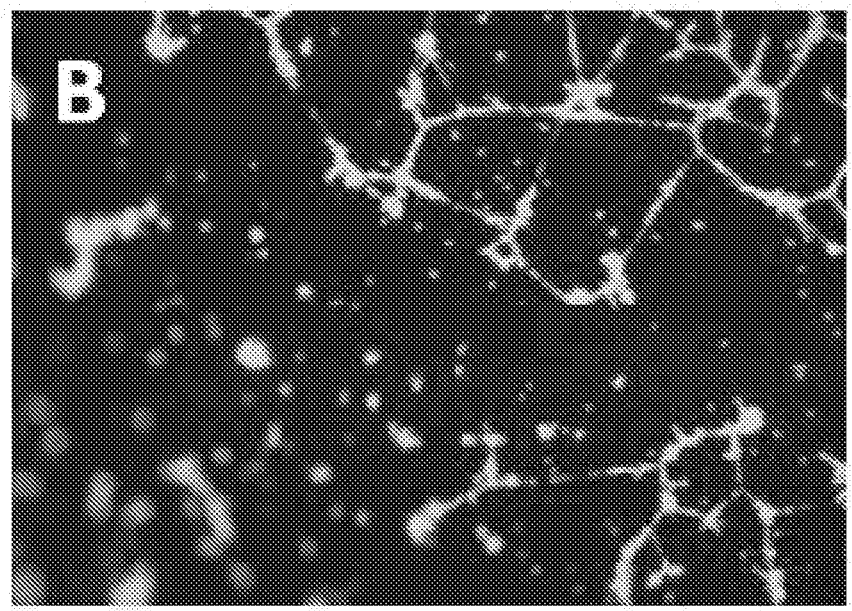

FACS analysis showed that cultured alveolar stem/progenitor cells expressed Stro-1, CD105, CD73, CD44 and CD90, but were negative to CD34 (see e.g., FIG. 1A). Alveolar stem/progenitor cells were differentiated osteoblasts, adipocytes, chondrocytes and myocytes per staining with von Kossa, Oil-red O, safrarin O, and myosin heavy chain (see e.g., FIGS. 1B-E, respectively). Transwell Migration assay showed that PDGF, especially PDGF-BB, induces robust, dose-dependent migration. FACS analysis showed that alveolar stem/progenitor cells expressed both PDGFR-A and PDGF-B (see e.g., FIG. 2). Alveolar stem/progenitor cells further differentiated into endothelial-like cells in chemically defined medium, formed classic three-dimensional capillary structure on matrigel (see e.g., FIG. 3).

Example 2

The following examples shows cartilage formation facilitated by cell homing. Such an approach can be used in a medical procedure such as Rhinoplasty.

Bilayered scaffolds were fabricated with a bottom poly (lactide-co-glycolic acid) (PLGA) layer and a top alginate layer containing gelatin microspheres that slow-release SDF1, TGFβ3, IGF1 and PDGFBB. Scaffolds were implanted in the subcutaneous nasal dorsum of 12 week old Sprague Dawley rats (see e.g., FIG. 4). Scaffolds were harvested after 10 weeks of implantation.

Figure 5:
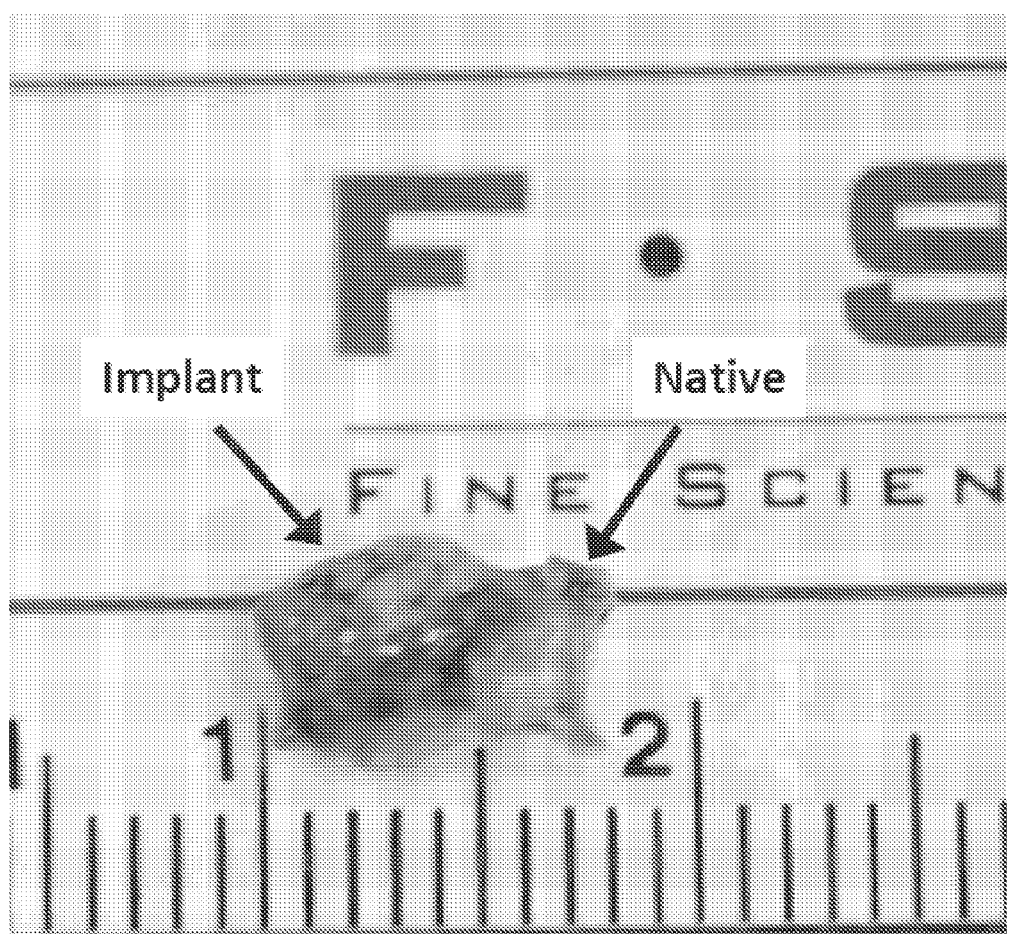
FIG. 5 is an image of a scaffold implanted in the subcutaneous nasal dorsum of a 12 week old Sprague Dawley rats and harvested after 10 weeks of implantation, well-integrated with native nasal cartilage tissue.
Figure 6C:
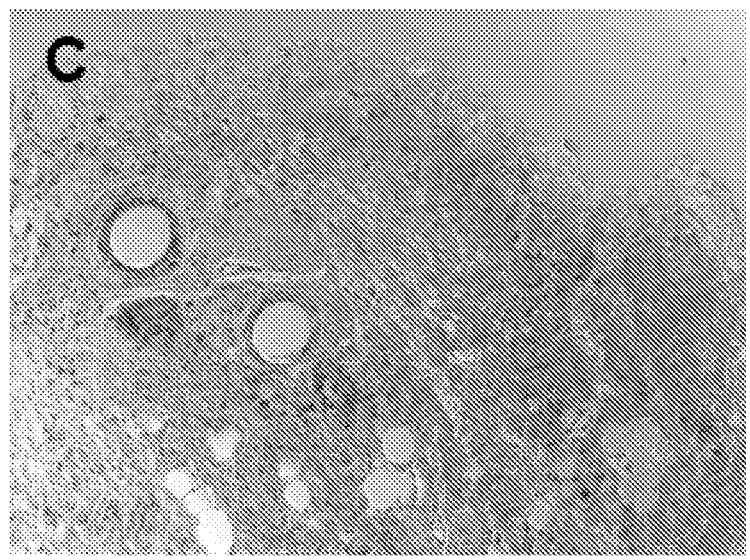
FIG. 6C shows Scaffold 3.
Figure 7:
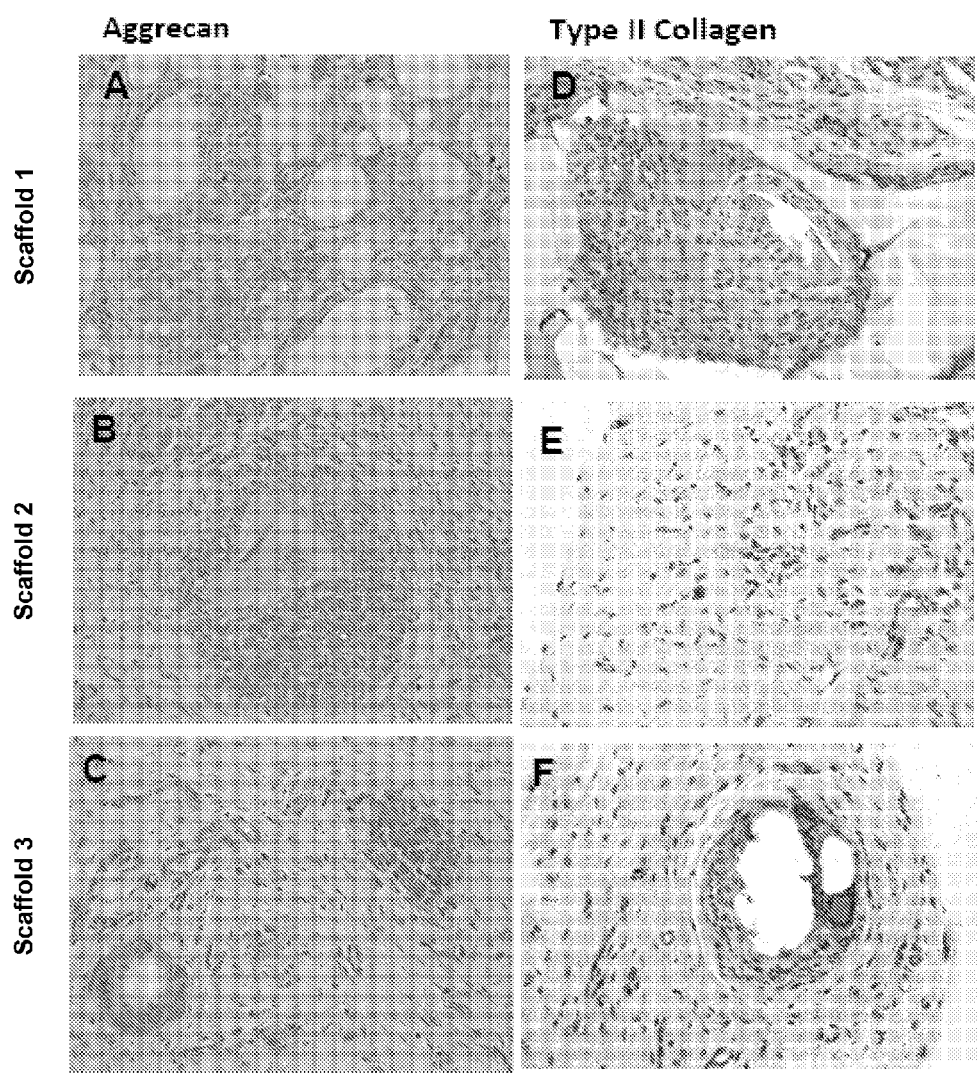
FIG. 7 is a series of immunohistochemistry images showing engineered tissue expression of cartilage specific markers for aggrecan and type II collagen.

Results showed that a large ectopic tissue was formed by the scaffold, which appeared to be well-integrated with native nasal cartilage tissue (see e.g., FIG. 5). An abundant number of cells were recruited into the scaffolds to form the engineered tissue (see e.g., FIG. 6). Engineered tissue expressed cartilage specific markers for aggrecan and type II collagen as shown by immunohistochemistry (see e.g., FIG. 7).

What is claimed is:

1. A method of treating a subject having tissue damage, the method comprising:
   implanting a scaffold comprising an effective amount of platelet-derived growth factor-BB (PDGF-BB) at or near a damaged tissue selected from damaged dental pulp or damaged dentin;
   wherein,
   the scaffold comprises fibrin or collagen;
   the scaffold does not comprise a transplanted cell prior to implantation in the subject;
   the PDGF-BB is present in the scaffold at a concentration of about 10 ng/ml to 1,000 ng/ml; and
   the effective amount of PDGF-BB recruits alveolar stem cells into the scaffold to regenerate dental pulp or dentin at or near the damaged tissue.

2. The method of claim 1, wherein the scaffold further comprises at least one of PDGF-AA and PDGF-AB.

3. The method of claim 1, wherein the scaffold comprises a composition comprising PDGF-BB and the PDGF-BB is present in the composition at a concentration of about 10 ng/ml to about 100 ng/ml.

4. The method of claim 1, wherein the scaffold comprises a composition comprising PDGF-BB and the PDGF-BB is present in the composition at a concentration of 250 ng/ml.

5. The method of claim 1, wherein the scaffold comprises at least two layers.

6. The method of claim 5, wherein at least one layer comprises PDGF-BB.

7. The method of claim 6, wherein the PDGF-BB is encapsulated in a microsphere.

8. The method of claim 1, wherein the PDGF-BB is encapsulated in a microsphere.

9. The method of claim 1, wherein the scaffold does not contain a bioactive molecule other than PDGF-BB.

10. The method of claim 1, wherein the scaffold does not contain an additional chemotactic growth factor, osteogenic growth factor, dentinogenic growth factor, amelogenic growth factor, or cementogenic growth factor.

11. The method of claim 1, wherein the scaffold further comprises an osteogenic growth factor, dentinogenic growth factor, amelogenic growth factor, or cementogenic growth factor.

12. The method of claim 1, wherein dental pulp and dentin are regenerated at or near the dental tissue defect.

13. The method of claim 1, wherein the scaffold comprises collagen in a substantially gelled phase.

14. The method of claim 1, wherein the scaffold comprises collagen gel.

15. The method of claim 1, wherein PDGF-BB is present in the scaffold at a concentration of about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 250 ng/ml, or about 300 ng/ml.

* * * * *

UNITED STATES PATENT AND TRADEMARK OFFICE
CERTIFICATE OF CORRECTION

| | | |
|---|---|---|
| PATENT NO. | : 9,603,899 B2 | Page 1 of 1 |
| APPLICATION NO. | : 13/877272 | |
| DATED | : March 28, 2017 | |
| INVENTOR(S) | : Jeremy J. Mao et al. | |

It is certified that error appears in the above-identified patent and that said Letters Patent is hereby corrected as shown below:

In the Specification

Column 1, Lines 15-17 should read:
-- This invention was made with government support under grant DE018248 awarded by the National Institutes of Health. The government has certain rights in this invention. --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*